(12) United States Patent
Muenster et al.

(10) Patent No.: US 10,216,866 B2
(45) Date of Patent: Feb. 26, 2019

(54) IMAGE RECONSTRUCTION BASED ON PARAMETRIC MODELS

(75) Inventors: Matthias Muenster, Wiesbaden (DE); Pia Dreiseitel, Eschborn (DE)

(73) Assignee: Smiths Heimann GMBH, Weisbaden (DE)

( * ) Notice: Subject to any disclaimer, the term of this patent is extended or adjusted under 35 U.S.C. 154(b) by 1155 days.

(21) Appl. No.: 14/000,907

(22) PCT Filed: Feb. 23, 2012

(86) PCT No.: PCT/IB2012/000416
§ 371 (c)(1),
(2), (4) Date: Mar. 28, 2014

(87) PCT Pub. No.: WO2012/114199
PCT Pub. Date: Aug. 30, 2012

(65) Prior Publication Data
US 2014/0222385 A1    Aug. 7, 2014

Related U.S. Application Data

(60) Provisional application No. 61/446,558, filed on Feb. 25, 2011.

(51) Int. Cl.
*G06F 17/50* (2006.01)
*G01N 23/046* (2018.01)
(Continued)

(52) U.S. Cl.
CPC ............ *G06F 17/50* (2013.01); *A61B 6/5205* (2013.01); *G01N 23/046* (2013.01);
(Continued)

(58) Field of Classification Search
CPC ..... G06F 17/50; A61B 6/5205; A61B 6/0471; A61B 6/4014; G01N 23/046; G06T 11/006; G06T 17/30
(Continued)

(56) References Cited

U.S. PATENT DOCUMENTS

| | | | | |
|---|---|---|---|---|
| 4,888,693 A | * | 12/1989 | Tam | ........................ A61B 6/08 378/4 |
| 6,201,888 B1 | * | 3/2001 | Kalvin | .................. G06T 7/0012 250/363.04 |

(Continued)

FOREIGN PATENT DOCUMENTS

EP    1612734 A2    1/2006

OTHER PUBLICATIONS

Thomsen_2005 (Thomsen V., Tutorial: Attenuation of X-Rays by Matter, Spectroscopy, vol. 20, Issue 9).*

(Continued)

*Primary Examiner* — Brian S Cook
(74) *Attorney, Agent, or Firm* — Finnegan, Henderson, Farabow, Garrett & Dunner, LLP

(57) ABSTRACT

Systems and methods for modeling are provided. The method can include acquiring scan data associated with a plurality of x-ray projections of an item. The method can further include determining at least one closed boundary curve associated with the item. For example, the method can determine a first maximum area based on the scan data and determine at least one edge of the first maximum area. The method can further generate a model of the item using the closed boundary curve and a first material specific parameter for a material within the closed boundary curve. The method can utilize the model to generate computed scan data, compare the computed scan data to the scan data, and determine a goodness of fit. The method can further adjust the model of the item by altering at least one of the closed boundary curve and the material specific parameter.

69 Claims, 10 Drawing Sheets

(51) Int. Cl.
*A61B 6/00* (2006.01)
*G06T 11/00* (2006.01)
*G06T 17/30* (2006.01)
*A61B 6/04* (2006.01)

(52) U.S. Cl.
CPC ............ *G06T 11/006* (2013.01); *G06T 17/30* (2013.01); *A61B 6/0471* (2013.01); *A61B 6/4014* (2013.01); *A61B 6/482* (2013.01); *F04C 2270/041* (2013.01); *G01N 2223/401* (2013.01); *G01N 2223/419* (2013.01)

(58) Field of Classification Search
USPC .......................................................... 703/6
See application file for complete search history.

(56) References Cited

U.S. PATENT DOCUMENTS

| | | | | |
|---|---|---|---|---|
| 8,879,791 B2* | 11/2014 | Drouin | ................. | G01N 23/046 378/57 |
| 2006/0170679 A1* | 8/2006 | Wang | ...................... | G06T 17/00 345/424 |
| 2009/0052762 A1* | 2/2009 | Dugan | ................... | G01N 23/06 382/132 |
| 2009/0146061 A1* | 6/2009 | Manneschi | ........ | G01N 21/9027 250/339.12 |
| 2010/0208972 A1* | 8/2010 | Bouchard | ............. | G01F 23/288 382/132 |
| 2010/0284514 A1* | 11/2010 | Zhang | ...................... | G01V 5/00 378/53 |

OTHER PUBLICATIONS

Feng_2003 (Feng, H., A Curve Evolution Approach to Object-Based Tomographic Reconstruction, IEEE Transaction on Image Processing, vol. 12, No. 1 Jan. 2003).*
The Randomhouse College Dictionary, 1972.*
Scavino_2009 (Application of automated imaging analysis to the identification and extraction of recyclable plastic bottles, Journal of Zhejiang University Science A 2009 10(6):794-799).*
Haff_2008 (X-ray detection of defects and contaminants in the food industry, Sens. & Instrumen. Food Qual. (2008) 2:262-273).*
Heuft (Empty Bottle Inspection: HEUFT InLine, HMDIRP101 ENG 2.01) pub date not available/unknown.*
International Search Report from corresponding PCT Application No. PCT/IB2012/000416 dated Sep. 11, 2012 (3 pages total).

* cited by examiner

IMAGE RECONSTRUCTION BASED ON PARAMETRIC MODELS

This application claims priority to U.S. Provisional Patent Application No. 61/446,558 filed Feb. 25, 2011, the contents of which are incorporated herein by reference.

DESCRIPTION

Technical Field

Systems, methods, and computer-readable products consistent with the present invention are directed generally to image reconstruction, and more particularly to image reconstruction based on parametric models.

Background

Baggage scanners can be used for baggage inspection, for example, at an airport or a train station, to detect the presence of liquid and other prohibited objects in baggage or luggage. For example, baggage scanners can be employed at airports and can include one or more sets of stationary x-ray scanning arrays. A set of x-ray scanning arrays can contain one or more radiation sources that are configured to emit x-ray radiation towards an item under inspection, and an array of detectors on the opposite side of the item to detect the x-ray radiation that is not completely absorbed by the item.

SUMMARY

In one aspect, the present disclosure is directed to a method of modeling. The method can include acquiring scan data, wherein the scan data comprises data associated with a plurality of x-ray projections of an item. The method can further include determining at least one closed boundary curve associated with the item. For example, the method can determine a first maximum area based on the data associated with the plurality of x-ray projections and determine at least one edge of the first maximum area. The method can further generate a model of the item using the closed boundary curve and a set of material specific parameters including at least a first material specific parameter, for a material within the closed boundary curve. The method can utilize the model to generate computed scan data, compare the computed scan data to the scan data, and determine a goodness of fit. The method can further adjust the model of the item by altering at least one of the set of: the at least one closed boundary curve and the set of material specific parameters including at least the first material specific parameter.

In another aspect, the present disclosure is directed to a system. The system can include a scanner configured to acquire scan data, wherein the scan data comprises data associated with a plurality of x-ray projections of an item. The system can further include a processor configured to determine at least one closed boundary curve associated with the item. For example, the processor can determine a first maximum area based on the data associated with the plurality of x-ray projections and determine at least one edge of the first maximum area. The processor can further generate a model of the item using the closed boundary curve and a first material specific parameter for a material within the closed boundary curve. The processor can utilize the model to generate computed scan data, compare the computed scan data to the scan data, and determine a goodness of fit. The processor can further adjust the model of the item by altering at least one of the set of: the at least one closed boundary curve and the material specific parameter.

In another aspect, the present disclosure is directed to computer-readable medium comprising instructions stored thereon, wherein the instructions cause a computer to perform a method of modeling. The method can include acquiring scan data, wherein the scan data comprises data associated with a plurality of x-ray projections of an item. The method can further include determining at least one closed boundary curve associated with the item. For example, the method can determine a first maximum area based on the data associated with the plurality of x-ray projections and determine at least one edge of the first maximum area. The method can further generate a model of the item using the closed boundary curve and a first material specific parameter for a material within the closed boundary curve. The method can utilize the model to generate computed scan data, compare the computed scan data to the scan data, and determine a goodness of fit. The method can further adjust the model of the item by altering at least one of the set of the at least one closed boundary curve and the material specific parameter.

DETAILED DESCRIPTION

Figure 1:
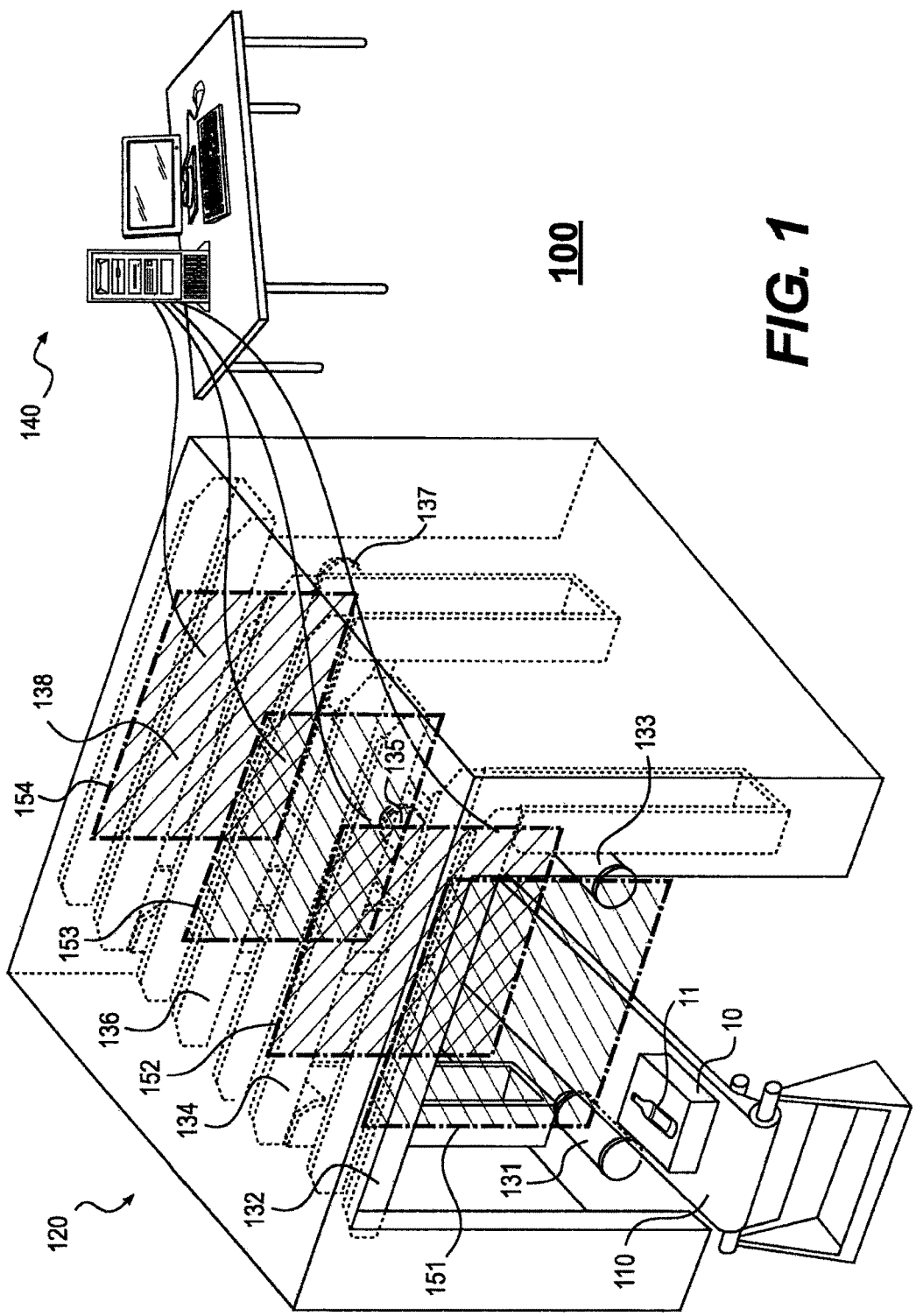
FIG. 1 is a schematic diagram of an inspection system consistent with an exemplary embodiment of the present invention.

FIG. 1 is a schematic diagram of an inspection system 100 according to an exemplary embodiment of the present disclosure. The inspection system 100 can be configured to inspect a container 10 and detect any material or object of interest contained in the container 10. For example, container 10 can be a crate, bag, box, or item of luggage. The container 10 can be any item that is to be transported by an airplane, sea vessel, train, or other mode of conveyance or into or within infrastructure, which can contain a plurality of objects such as clothes, shoes, electronic devices, books, etc. The container 10 also can contain an item 11 exhibiting a certain shape. For example, the item 11 can be a bottle of wine or water, a can of beverage, a bottle of liquid explosives, a boxed juice, a bottle of shampoo or conditioner, and the like. For example, FIG. 1 shows an item 11 in the container 10.

The item 11 can include two or more materials. For example, the item 11 can be a bottle of wine that includes a glass bottle and wine therein. When the bottle is not completely filled with wine, there can also be air in the bottle. In one embodiment, the inspection system 100 can be employed at a security check point for checked baggage or carry-on baggage at an airport to detect these objects of interest or materials in the container 10. While the above example relates to a bottle of wine, it is contemplated that the inspection system 100 can be employed to detect any object of interest or material in any item capable of being scanned and yielding material-specific information.

The inspection system 100 can include a conveyor 110, a scanner 120, and a data processing system 140 coupled to scanner 120. The conveyor 110 can include belts for supporting the container 10 and one or more motors that drive the belts. The belts can rotate intermittently or continuously to convey or provide the container 10 from a loading area through a central aperture of the scanner 120. The conveyor 110 is illustrated as including a plurality of individual conveyor sections in FIG. 1; however, it is contemplated that other forms of conveyors can be used.

The scanner 120 can be any suitable scanner. For example, the scanner 120 can include multiple sets of x-ray source and detector arrays. As illustrated in FIG. 1, the scanner 120 can include, among other things, four sets of source and detector arrays, including x-ray sources 131, 133, 135, and 137, and x-ray detector arrays 132, 134, 136, and 138. It is contemplated that the scanner 120 can include more or less sets of source and detector arrays as depicted in FIG. 1. In some embodiments, any one of—or all of—the x-ray sources 131, 133, 135, and 137 can be a point source, and any of the x-ray detector arrays 132, 134, 136, and 138 can present an array of detectors arranged substantially along a line, or substantially along two lines that intersect at a right angle—as is depicted in FIG. 1. In some embodiments, the x-ray detector arrays 132, 134, 136, and 138 can present an array of detectors arranged substantially along a curve or other path, or combinations of such paths. The x-ray sources 131, 133, 135, and 137 and the x-ray detector arrays 132, 134, 136, and 138 can be mounted, stationary, and arranged such that a respective x-ray source and corresponding detector array are on opposite sides of the aperture through which the container 10 is conveyed. Although FIG. 1 shows the aperture in a substantially square shape, it is contemplated that the aperture can be of any other suitable shape, such as, for example, a substantially circular or oval shape or a substantially rectangular shape, or any combination thereof.

The x-ray sources 131, 133, 135, and 137 and x-ray detector arrays 132, 134, 136, and 138 can be located at different positions along the length of the conveyor 110. Accordingly, when the container 10 is displaced through the aperture by operation of the conveyor 110, it can sequentially pass through a plurality of scanning planes 151, 152, 153, and 154. In some embodiments, the separation between successive scanning planes (as between scanning plane 151 and 152) can be approximately 20 cm.

As described above, each combination of x-ray source and detector array, such as a combination including one of the x-ray sources 131, 133, 135, and 137, and one of the detector arrays 132, 134, 136, and 138, can define a scanning plane (respectively, scanning plane 151, 152, 153, and 154 in FIG. 1). Each of the x-ray sources 131, 133, 135, and 137 can generate a fan beam of x-ray radiation over a fan-shaped two-dimensional cross-section through which the container 10 can pass. The x-ray beams within the respective scanning planes can pass through and be partially attenuated by the container 10 and then received by the corresponding x-ray detector array associated with that scanning plane. In some embodiments, the x-ray sources 131, 133, 135, and 137 can be oriented to direct the fan-shaped beam in different directions (relative to each other), and as a result, radiation data associated with different projection angles can be obtained from the x-ray detector arrays 132, 134, 136, and 138.

Figure 2:
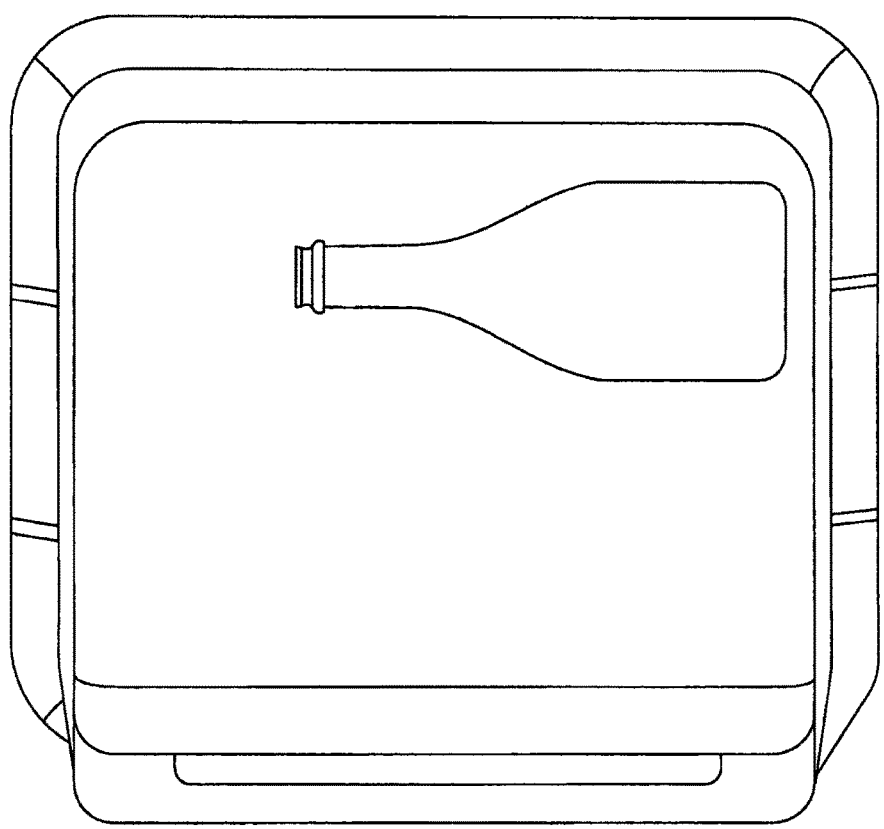
FIG. 2 shows a two-dimensional projection image of a bottle of wine.

As used herein, the radiation data acquired by an x-ray detector array is referred to as "projection data," and the perspective defined by the uniform cross-section intersecting with the scanned item is referred to as a "projection perspective." During a scan, the x-ray detector arrays can collect multiple sets of projection data representative of the integral of absorption coefficients of the volumetric segment of container 10 through which the x-ray beams pass. The measurement of projection data can be used to form a raster line of a two-dimensional projection image. For example, FIG. 2 shows a two-dimensional projection image of a bottle of wine in a tray.

A plurality of projection views of the container 10 at different projection perspectives can be generated and a corresponding plurality of sets of two-dimensional projection data can be acquired by the x-ray detector arrays 132, 134, 136, and 138. Although the image in FIG. 2 shows only one "view" of the item, other views can be obtained by other detector arrays simultaneously and/or sequentially.

In an embodiment, the scanner 120 can be a multi-energy scanner. For example, in a source-detector-array set, x-ray beams can be generated at different energy levels, by multiple x-ray sources or by a single source that operates in a switched manner. In some embodiments, multi-energy scanning can be performed using a broad spectrum x-ray source and x-ray detector arrays that detect x-ray radiation in separate energy ranges. For example, in a dual energy scanner, Hi and Low scan data can be collected by each detector array.

The x-ray detector arrays 132, 134, 136, and 138 can be coupled with data processing system 140 via one or more data transmission lines. Multi-angle projection data acquired by the scanner 120 can be transferred to a data processing system 140 via the data transmission lines. The projection data can also be transferred wirelessly to the data processing system 140.

The data processing system 140 can include one or more computer assemblies configured to analyze scan data acquired from the scanner 120 and associated with a scan of an item exhibiting a certain shape or a material contained therein, such as a liquid material, in the container 10. The data processing system 140 can be associated with one or more software applications, including, for example, an image reconstruction tool. These software applications can be stored on the data processing system 140, and can be accessed by an authorized user, such as an operator at a customs, ports and borders control, or airport. The software applications also can be stored on a computer readable medium, such as a hard drive, computer disk, CD-ROM, or any other suitable medium.

Figure 3:
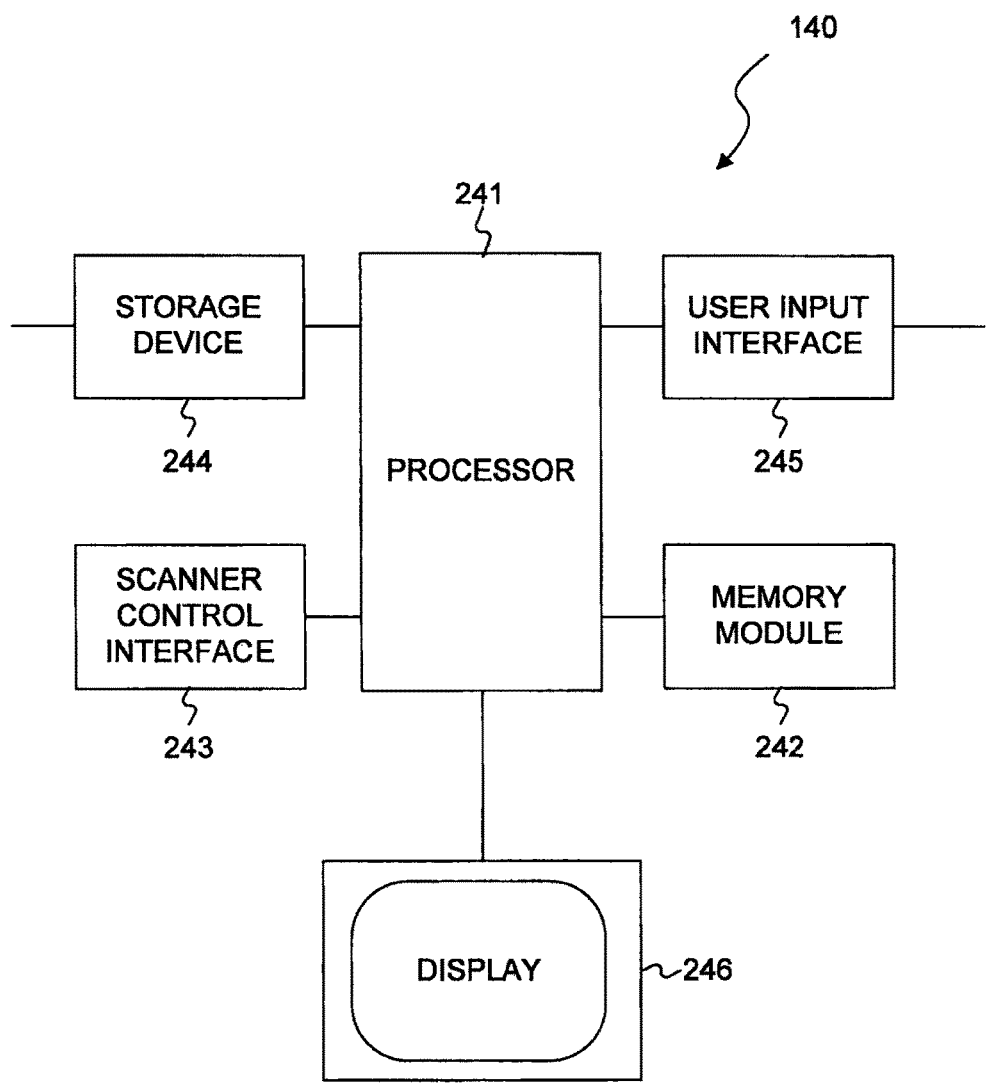
FIG. 3 is a schematic diagram of a data processing system, consistent with the exemplary disclosed embodiment shown in FIG. 1.

FIG. 3 is a schematic diagram of the data processing system 140. The data processing system 140 can include a processor 241, a memory module 242, a scanner control interface 243, a storage device 244, an input/output interface 245, and a display device 246. The data processing system 140 can include additional, fewer, and/or different components than those listed above. The type and number of listed devices are exemplary only and not intended to be limiting.

The processor 241 can be a central processing unit ("CPU") or a graphic processing unit ("GPU"). The processor 241 can execute sequences of computer program instructions to perform various processes that will be explained in greater detail below. The memory module 242 can include, among other things, a random access memory ("RAM") and a read-only memory ("ROM"). The computer program instructions can be accessed and read from the ROM, or any other suitable memory location, and loaded into the RAM for execution by the processor 241. The processor 241 can include one or more printed circuit boards, and/or a microprocessor chip.

The scanner control interface 243 can be configured for two way communication between the scanner 120 and the data processing system 140. Consistent with one embodiment, the scanner control interface 243 can be configured to receive scan data from the scanner 120 and store the data into the storage device 244. The scanner control interface 243 can be further configured to send scan control instructions to the scanner 120 to initiate and stop scan operations, or to configure the scanners. For example, the scan control instructions can include configuration parameters.

The storage device 244 can include any type of mass storage suitable for storing information. For example, the storage device 244 can include one or more hard disk devices, optical disk devices, or any other storage devices that provide data storage space. For example, the storage device 244 can store data related to a data processing process, such as the processing of scan data received from the scanner 120, and any intermediate data created during the data processing process. The storage device 244 can also store one or more models and their associated parameters that can be used for assisting the data processing. For example, the storage device 244 can store a model of a generic object having a same or similar shape to an object of interest, e.g., the item 11 in the container 10. The model of the generic object may be used for reconstructing the image of the item 11. The storage device 244 can also include analysis and organization tools for analyzing and organizing data and/or information contained therein.

The data processing system 140 can be accessed and controlled by a user, such as a security officer, using the input/output interface 245. The input/output interface 245 can be available for the user to input information into data processing system 140, and can include, for example, a keyboard, a mouse, a touch screen and/or optical or wireless computer input devices. The user can input control instructions via the input/output interface 245 to control the operation of the conveyor 110, and/or the scanner 120. For example, the user can push certain buttons on a keyboard to stop the conveyor 110, instruct it to go in reverse (e.g., backwards), or resume going forward. The user can also input parameters to adjust the operation of the data processing system 140.

The data processing system 140 can also provide visualized information to the user via the display device 246. For example, the display device 246 can include a computer screen (not shown) and make available a graphical user interface ("GUI") to the user. The display device 246 can display an image of the item 11 and/or the container 10 in its entirety, such as a three-dimensional image, multiple projection images and/or a two-dimensional cross-section image. Consistent with another embodiment, the display device 246 can also display an inspection report to the user indicating certain characteristics of items contained in the container 10, such as a presence of bottled liquid, the type of liquid, and the volume of the liquid, in the container 10.

Figure 4:
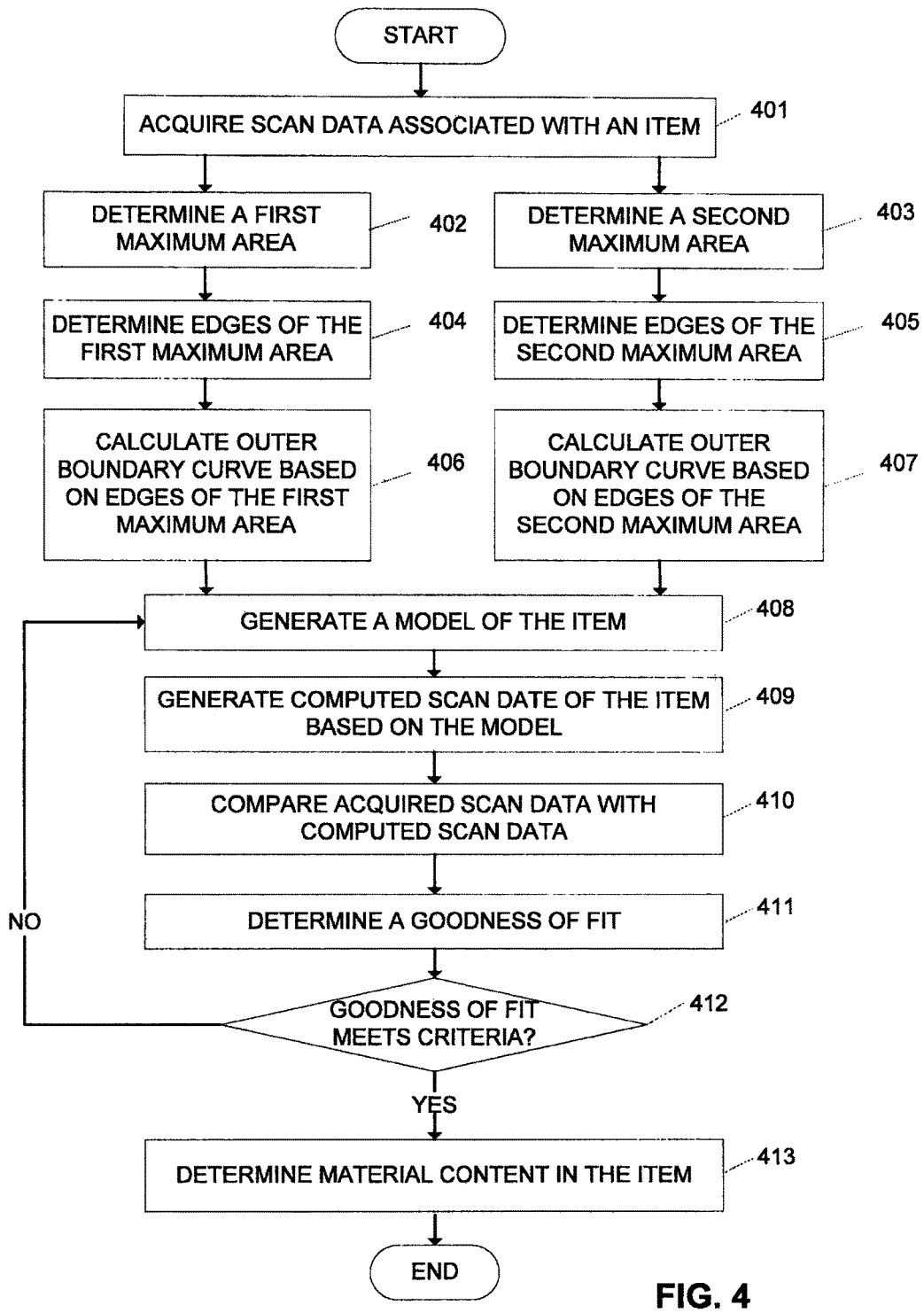
FIG. 4 is a flow chart of an exemplary process of analyzing an item, consistent with a disclosed embodiment.

One or more components of the inspection system 100 can be used to implement a process for analyzing the container 10 containing at least one object. FIG. 4 is a flow chart of an exemplary process of modeling a target item utilizing the inspection system 100. Scan data associated with an item, such as exemplary item 11, may be acquired (step 401). By way of example only, and without limitation, item 11 can be made available, inside the container 10, to the scanner 120 by the conveyor 110. An x-ray scan can be conducted on the item 11 by the scanner 120. During the scan, multiple sets of two-dimensional projection data can be acquired by multiple sets of x-ray source and detector arrays. The acquired projection data can be transferred to the data processing system 140.

The projection data can be used to reconstruct image slices perpendicular to the plane of the projection data and to determine one or more closed boundary curves associated with the item (steps 402-412). Any suitable image reconstruction methods, including, but not limited to, filtered back projection, Fourier reconstruction, and iterative reconstruction, can be used to transform the projection data and determine the one or more closed boundary curves. In one embodiment consistent with the present disclosure, the data processing system 140 can use a parametric image reconstruction method.

Figure 6:
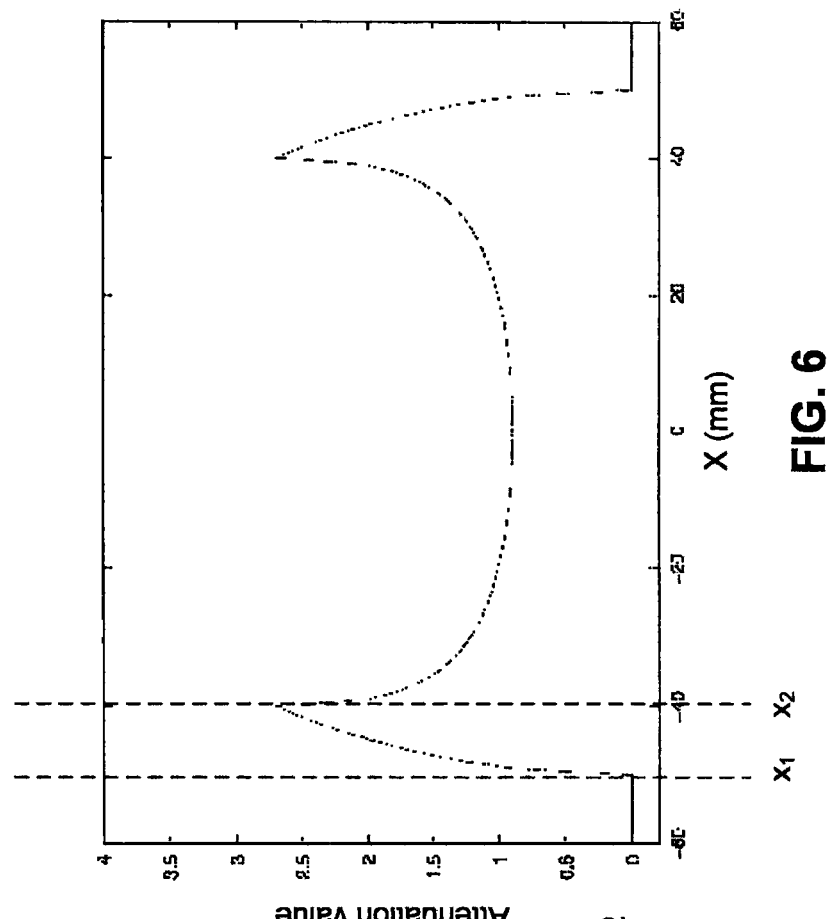
FIG. 6 is a chart illustrating projection data, obtained consistent with the exemplary embodiment of FIG. 8.
Figure 5:
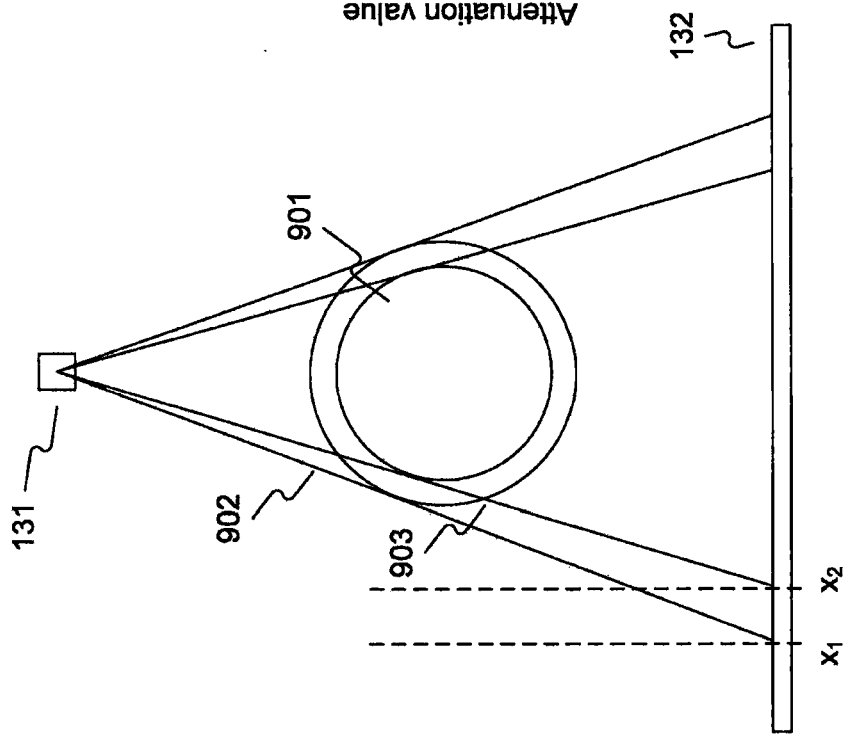
FIG. 5 is an illustration of x-rays tangential to the inner and outer boundary curves of an exemplary object.

For example, a first maximum area can be determined based on a combination of x-ray projections (step 402) and optionally, a second maximum area can also be determined (step 403). In some embodiments, the second maximum area may be completely inside of the first maximum area. As shown in FIG. 5, when a cross-section of a glass bottle 901 is scanned by the scanner 120, a fan beam x-ray pattern can be generated by the x-ray source 131. The x-ray beams can pass through and be partially attenuated by the glass bottle 901 of interest and then received by the x-ray detector array 132. FIG. 5 shows x-ray 902 and x-ray 903 that are tangential to the outer and inner boundary curves of the glass bottle 901. X-rays 902 and 903 can intersect with the x-ray detector array 132 at locations $x_1$ and $x_2$, respectively. The projection data received by the x-ray detector array 132 is shown in FIG. 6. It can be observed from FIG. 6, that the attenuation values to the left of location $x_1$ is close to 0, and once past $x_1$, the attenuation value increases dramatically to a peak value around location $x_2$, after which, the attenuation value starts to decrease. Therefore, locations $x_1$ and $x_2$ can be found based on the projection data, and the tangential x-rays can be identified by projecting the x-rays from locations $x_1$ and $x_2$ back to the x-ray source 131. As shown in FIG. 5, four tangential x-rays can be identified from projection data of each projection angle.

Figure 7:
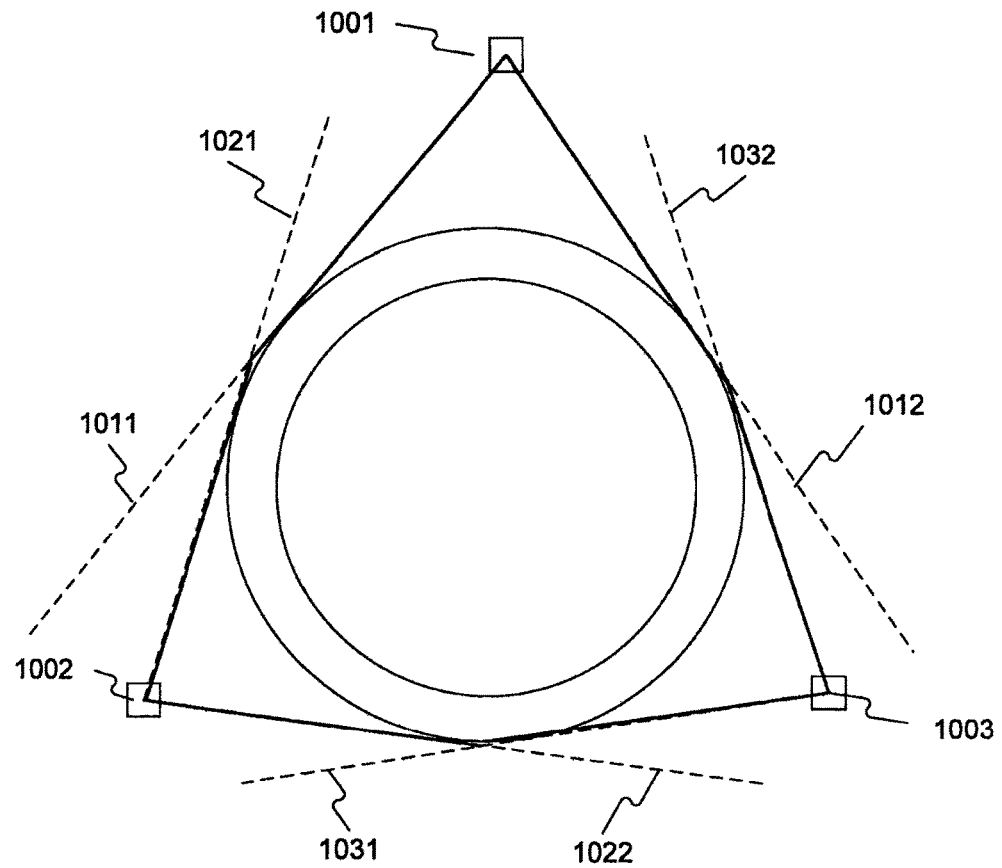
FIG. 7 illustrates convex polygon formed by tangential x-rays, consistent with an exemplary embodiment using three point x-ray sources.

When sufficient tangential x-rays are determined as described above, they can be used to form two maximum areas: a first maximum area associated with the outer boundary and a second maximum area associated with the inner boundary. For example, one or more of maximum areas can be in the shape of a convex polygon, such as shown in FIG. 7. As illustrated in FIG. 7, three point x-ray sources 1001-1003 can be used in the scanner 120. In one embodiment, x-ray sources 1001-1003 can correspond to any three of the x-ray sources 131, 133, 135, and 137 depicted in FIG. 1. As described above, tangential x-rays 1011 and 1012 can be identified for source 1001, tangential x-rays 1021 and 1022 can be identified for source 1002, and tangential x-rays 1031 and 1032 can be identified for source 1003, respectively. A convex polygon, as the one shown in bold lines, can be formed using the tangential x-rays and intersections thereof. Another convex polygon can be formed in a similar manner for the inner boundary curve.

Once the maximum areas are determined, one or more edges of the maximum areas can be determined (steps 404 and 405). For example, the edges may be detected by applying image processing methods to the area as shown in FIG. 7. An outer boundary curve can be determined based on the edges of the first maximum area (step 406) and an inner boundary curve may be determined based on the edges of the second maximum area (step 407). In one embodiment, the convex polygons become the inner and outer boundary curves of the item.

In another embodiment, solutions closer to the real boundary curves can be generated, e.g. by fitting a simplified model comprising two concentric ellipses, into the convex polygons. The two concentric ellipses can be uniquely determined by a total of six parameters: the coordinates ($m_x$, $m_y$) of the common center point of the two ellipses, the radii ($r_x$, $r_y$) of the main axis of the outer ellipse, the thickness of the glass d as well as the angle of rotation $\phi$. The fitting process can be implemented using optimization approaches, such as, for example, Simulated Annealing (SA). During the optimization, the sum of the squares of the smallest distances between the tangential x-rays and the associated ellipse can be minimized. Once determined, the two concentric ellipses, instead of the convex polygons, become the inner and outer boundary curves of the item.

Figure 8:
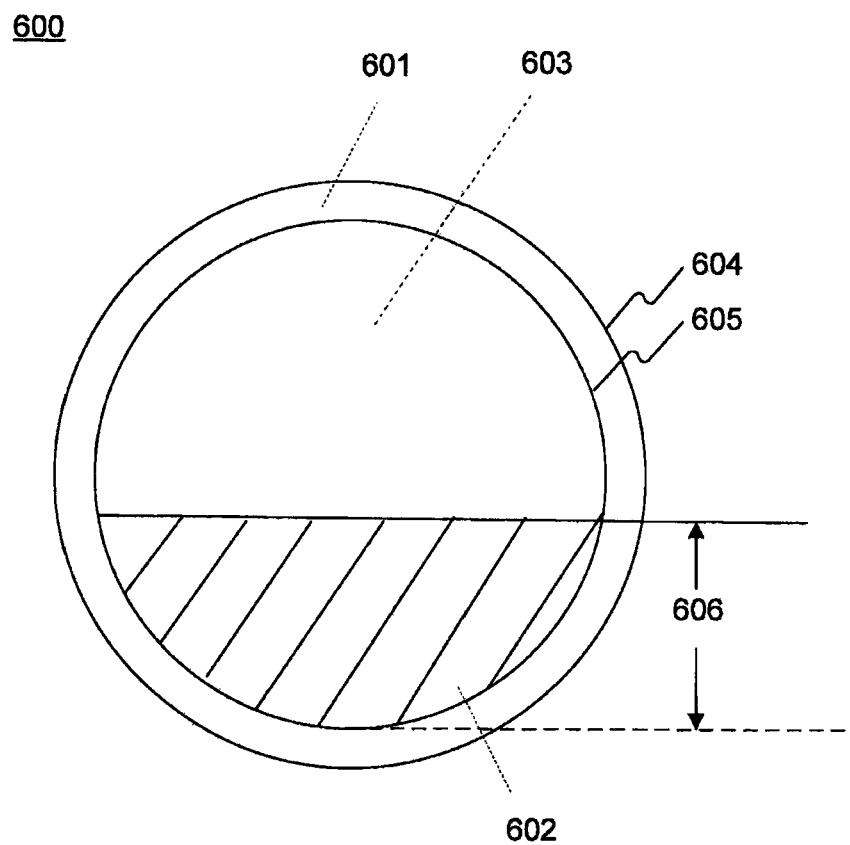
FIG. 8 is a schematic diagram of an exemplary parametric model of a cross-section of a cylindrical container, consistent with a disclosed embodiment.

A model of the item can be generated (step 408). The model can depend upon a set of parameters. In some embodiments, the parametric model can include the inner and outer boundary curves determined in steps 406-407, and a set of material specific parameters including one or more material specific parameters. For example, FIG. 8 is a schematic illustration associated with a parametric model 600 of a cross-section of a cylindrical item that exhibits two closed boundary curves. In some embodiments, model 600 can be described by a set of material specific parameters, including a first material specific parameter of the receptacle material 601. In some embodiments, model 600 can be further described by a second material specific parameter of the material content 602 in the receptacle. For example, the item may be a bottle filled with liquid. In this example, the first material specific parameter can be an x-ray absorption coefficient of glass, plastic or any other receptacle material 601. The second material specific parameter can be an x-ray absorption coefficient of alcohol, water, or any other material content 602. In one embodiment, the model 600 can further include a third material specific parameter corresponding to material content 603, such as air.

Model 600 can also include a set of shape parameters describing the two closed boundary curves. For example, model 600 may include an outer curvature 604 of the container and an inner curvature 605 of the container. In some embodiments, outer curvature 604 and inner curvature 605 can be of a same shape or two different shapes, including circular, oval, square, rectangular, or any other suitable shapes. For example, the boundary curves 604 and 605 can be approximated by two ellipses, which have corresponding center points and angles of rotation. Accordingly, the radii of the two ellipses can differ in the direction of the major axis by the thickness of the container. Furthermore, for example, each boundary curve can also be approximated by a polygon whose shape can be determined by a set of points. Examples of this explicit representation can be found in published work e.g. Soussen et al., "Polygonal and Polyhedral Contour Reconstruction in Computed Tomography", IEEE Transactions on Image Processing, vol. 13, no. 11, pp. 1507-1523, November 2004. In some embodiments, an implicit, level-set based representation of the boundary curve, similarly to that of Feng et al., "A Curve Evolution Approach to Object-Based Tomographic Reconstruction", IEEE Transactions on Image Processing, vol. 12, no. 1, pp. 44-57, January 2003, could alternatively be used.

In one embodiment, the model 600 can further include a third boundary curve that is either closed or open, such as the upper surface of the material content in the receptacle. Accordingly, the set of shape parameters can further include a maximal distance 606 between at least two distal boundaries of the material contents. As illustrated in FIG. 8, the maximal distance 606 can be the distance between this flat surface and the lowest point of the inner curvature of the closed boundary curve 605. In another embodiment the maximal distance can be the distance between this flat surface and the origin of the coordinate system. It is contemplated that the distal boundaries of the material content can be of any shape. Although the exemplary model illustrated in FIG. 8 is two-dimensional, it is contemplated that the model can be three-dimensional.

The set of parameters can be assigned a set of initial values. For example, the initial locations of the two closed boundary curves 604 and 605 can be determined as described above in steps 402-407. In one embodiment, the initial values of the material specific parameters can be set to a reasonable known value to start with. Alternatively, the initial values can also be selected based on a solution provided by a conventional image reconstruction method. For example, FBP or regularized iterative method can be employed to reconstruct the image first, and the solution may be used as the initial values. A library of initial values of the first material specific parameter and the second material specific parameter can be accessible to the processor 241.

In some embodiments, a set of material specific parameters of objects outside the outer boundary curve can also be determined concurrently in step 408. For example, another object other than the item 11 can be located in a region outside outer curvature of closed boundary curve 604 of the item 11 the x-ray absorption coefficients of this object can be determined as a voxel array based on the scan data. Any suitable reconstruction methods, such as the parametric reconstruction method, can be utilized for determining the voxel array.

Figure 9:
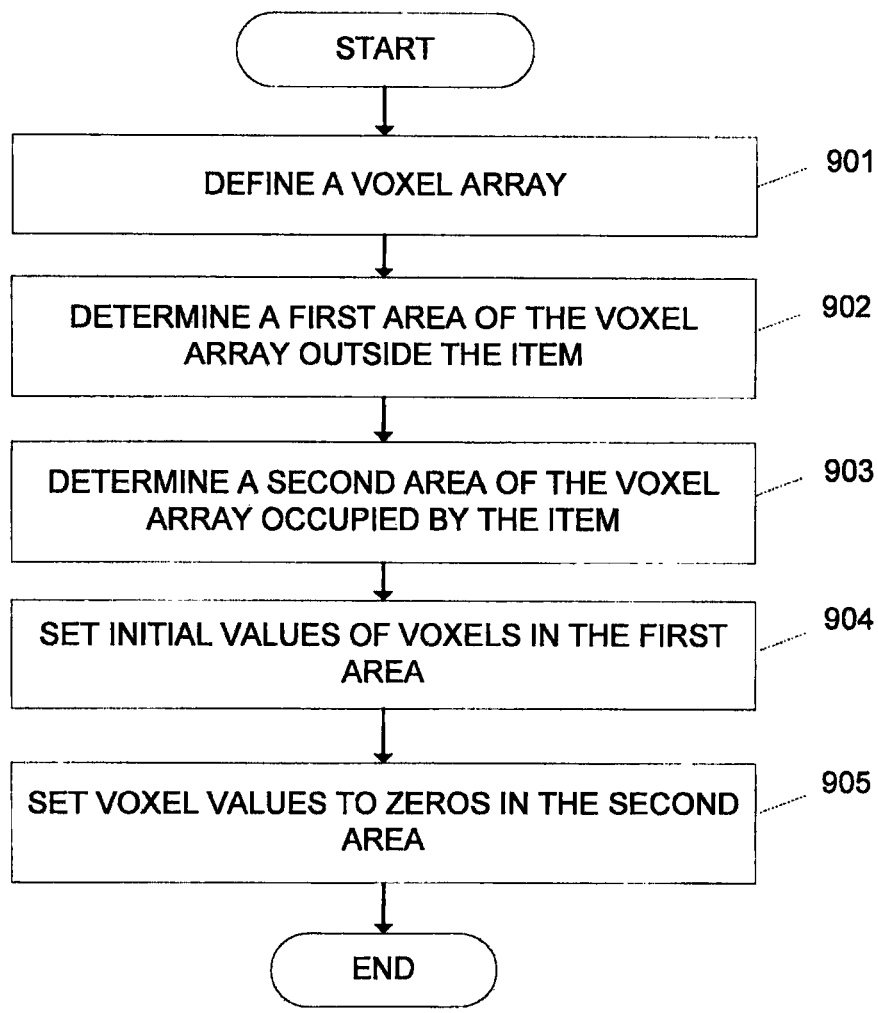
FIG. 9 is a flow chart of an exemplary process for initializing a voxel array, consistent with a disclosed embodiment.

FIG. 9 is a flow chart of an exemplary process for initializing a voxel array, consistent with a disclosed embodiment. A voxel array can be defined as a three-dimensional array representing the entire scan volume of the container 10 (step 901). Alternatively, in one embodiment, the voxel array can represent a single slice of the volume (that is, virtually a 2-D representation), For example, the value of each voxel may be associated with the x-ray absorption coefficient of a corresponding region in the scan volume. The voxel array can be segmented into two areas: a first area including voxels outside the item, and a second area including voxels that are occupied by the item (steps 902 and 903). For example, the voxel array can be estimated from the scan data using any existing image reconstruction method, and then the reconstructed image can be segmented using any existing image segmentation method.

Initial values can be set to the voxels in the first area (step 904). In some embodiments, the initial values can be set to be equal to those estimated from the scan data. The voxels in the second area can be set to zero (step 905). In some embodiments, the voxels in the second area can remain zero throughout the entire process shown in FIG. 4. For example, during each iteration, the values of voxels in the second area may be computed along with the values of voxels in the first area, and as a result, voxels in the second area may carry on values different than zero, but these values can be suppressed/forced to zero during the iteration.

Once a model is generated and the initial values for the model parameters are set, computed scan data can be generated based on the model (step 409). In some embodiment, the computed scan data can include multiple projections of the model based on the projection perspectives of the scanner 120. The computed data can be calculated, for example, using forward projection method.

The computed scan data can be compared with the scan data acquired in step 401 (step 410), and determine a goodness of fit based on the comparison (step 411). In some embodiments, the goodness of fit can be measured by a cost function that includes a data term assessing the difference between the computed scan data and acquired scan data. For example, the difference can be a Lp-Norm difference, where $1 \leq p \leq \infty$, or a Pseudo-Norm difference with p<1 between the computed scan data and acquired scan data. An exemplary cost function will be described in greater detail in connection with FIG. 10.

The determined goodness of fit can be compared against an iteration stopping criteria (step 412). In some embodiments, the iteration stopping criteria can be set as a sufficiently small number. The smaller the number is, however, the longer time the process may take to achieve convergence. If the goodness of fit does not meet the iteration stopping criteria (step 412: no), process may go back to step 408, and the model can be adjusted. For example, the inner closed boundary curve and the outer closed boundary curve, and/or any of the set of material specific parameters can be altered to adjust the model of the item. Steps 408-412 can be iteratively repeated until the goodness of fit meets the iteration stopping criteria.

Once the criteria is met (step 412: yes), the data processing system 140 can determine if the material specific parameter or the set of material specific parameters corresponds to a material specific parameter of a material that satisfies a further criteria. For example, and without limitation, further criteria can include a determination that the material is among a set of materials considered dangerous and therefore not allowed to be carried on an airplane (step 413).

In some embodiment, an indication that the material content 602 corresponds to a prohibited material can be included in an inspection report to the user. Based on the report, the user can choose to open the container 10 for a visual inspection if the report suggests that prohibited objects are contained in the item. The process can conclude after step 413.

Figure 10:
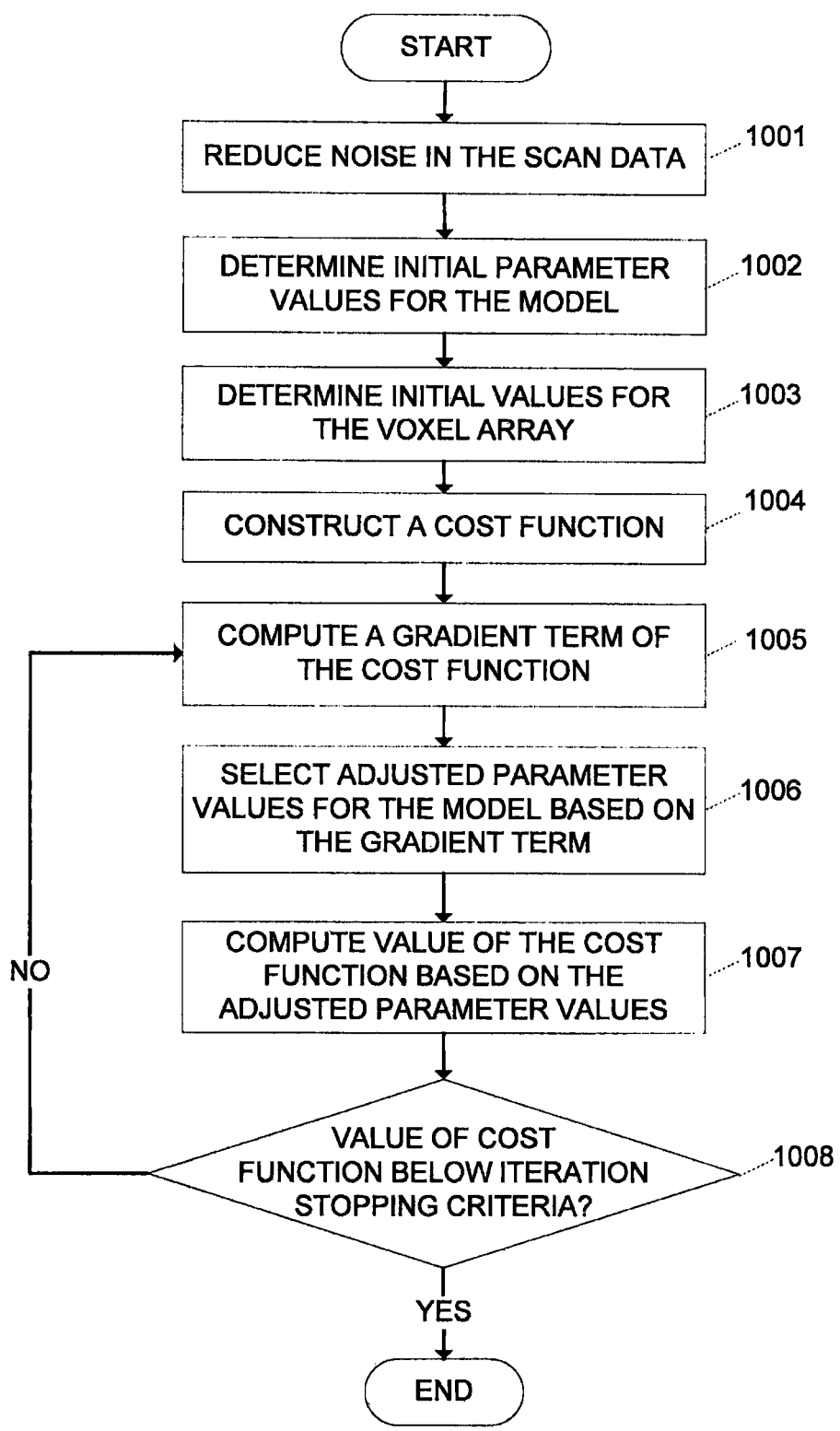
FIG. 10 is a flow chart of an exemplary process of parametric image reconstruction from projection data, consistent with a disclosed embodiment

FIG. 10 is a flow chart of an exemplary process of parametric image reconstruction from projection data, consistent with the present invention. The scan data acquired by the scanner 120 can have noise due to, e.g., scattering of x-ray beams, device inaccuracies associated with the detector arrays, and etc. Noisy data can impair the quality of a reconstructed image, especially when the scan data are under-sampled. In one embodiment, the scan data can be pre-processed to reduce noise (step 1001). For example, various filtering techniques can be used for noise reduction.

In particular, filtering can be conducted using an optimization approach. For example, the filtering can be based on optimizing an $L_2$-$L_1$ cost function:

$$C(\hat{b}) = \|b - \hat{b}\|_2^2 + \lambda \cdot |M \cdot \hat{b}\|_1^1, \tag{1}$$

where $\hat{b}$ is a vector of filtered scan data, b is a vector of the acquired scan data, and M is a matrix of a discrete gradient operator. In one embodiment, the M matrix can have a horizontal and a vertical component, calculated using forward differences.

The first term of Equation (1), also known as the data term, dictates a difference between the filtered scan data and the acquired scan data. It is formulated as a $L_2$-Norm under the assumption that scan data noise follows a Gaussian distribution. However, it is contemplated that the data term can also be formulated following a different noise distribution, such as a Poisson distribution. The second term, also known as the regularization term, dictates the total gradient of the acquired scan data. The regularization term preserves the boundaries of the scan data because of the application of the $L_1$-Norm. The regularization term used in Equation (1) is exemplary only, and it is contemplated that other types of $L_1$-regularization terms can also be used, such as a Total Variation (TV). The parameter $\lambda$ can determine the relative weight of the second term, i.e., the strength of the regularization.

The cost function of Equation (1) can be optimized using various iterative methods. For example, Equation (1) can be minimized with Iterative Coordinate Descent (ICD) method, which is effectively a Gauss-Seidel iteration. Using this method, in each iteration step, one data value is optimized while adjacent data values are held constant. It is contemplated that other suitable iterative methods, such as Conjugate Gradient (CG), can also be used. When multi-energy projection data are acquired from the scanner 120, the noise reduction step 1001 can be performed on the multiple channel scan data, such as the Hi and Low scan data individually. In one embodiment, the filtered multi-energy projection data can be broken down into a polyethylene (PE) portion of scan data and an aluminum (Al) portion of scan data to be employed during the projection bound identification process described above with respect to steps 402-407.

As described in connection with step 408, a parametric model, such as model 600 shown schematically in FIG. 8, can be constructed before iteratively reconstructing the image. Model 600 can depend on a set of parameters such as the material specific parameters associated with the receptacle material 601 and material content 602; 601-603 and the shape parameters associated with the closed boundary curves 604, 605 and the maximal distance 606; 604-606. The data processing system 140 may be configured to determine and set initial values for these parameters as a starting point of an iterative process (step 1002). In one embodiment, initial values may be selected based on prior knowledge about the item 11 in the container 10. For example, if the object is known to be a cylindrical bottle, the outer and inner curvatures of the closed boundary curves 604, 605 can be easily modeled as two circles.

In one embodiment, the estimated boundaries can be determined in two steps: (A) find the projection rays that are tangential to the inner and outer curvature of the container; and (B) use the projection rays found in (A) to construct two convex polygons as the estimated inner and outer boundaries.

Initial values can also be set for a voxel array (step 1003). For example, a voxel array can be defined and initialized as described above in connection with FIG. 9. In some embodiments, the voxels in the second area can be forced to zeros throughout the entire process shown in FIG. 10.

After the initial values for both the parametric model and the voxel array are set, the data processing system 140 can be further configured to construct a cost function for the reconstruction problem (step 1004). An exemplary cost function is given by Equation (2):

$$C(x, m_i, i = 0, \ldots, N_m - 1) = \left\| A \cdot x + \sum_{i=0}^{N_m-1} p(m_i) - b \right\|_2^2 + C_v(x) + \sum_{i=0}^{N_m-1} C_m(m_i), \quad (2)$$

where x is the voxel array, $m_i$ is a parameter vector of the i-th parametric model containing the position vectors of the inner and outer boundary curves 604 and 605, A is the voxel-related projection matrix, p( ) is a projection operator applied on the parametric model, b is a vector of scan data. The shape parameter vector $m_i$ of the i-th parametric model can be represented by Equation (3):

$$m_i = (\vec{p}_{i,0}^T, \ldots, \vec{p}_{i,2 \cdot N_e-1}^T, h_i, \mu_{g,i}, \mu_{l,i})^T \quad (3)$$

where $\vec{p}_{i,j}$ and $h_i$ are the shape parameters: $\vec{p}_{i,j}$ are the position vectors of the $2 \cdot N_e$ points on the inner and the outer boundary curves 604 and 605, and $h_i$ is the maximal distance parameter indicative of the filling level of the material content, and the material specific parameters $\mu_{g,i}$ and $\mu_{l,i}$, such as absorption values of the glass bottle and liquid filled therein. The first term of the cost function is a data term that assesses the deviation between the model-based projection data and the measured projection data, the second term and the third term are regularization terms that allows prior knowledge about the nature of the solution into the reconstruction process. The second term is a voxel/pixel value related regularization term, and the third term is a model-related regularization term. The voxel-related regularization term comprises three components, namely a term which penalizes voxel gradients, a term which supports the positivity of the values assigned to the voxels and finally a term which keeps the values of those voxels close to zero that are covered by any of the $N_m$ parametric models. Furthermore, each of the model related regularization terms hosts a component that tries to avoid an excessive local curvature along each of the boundary curves. A second component drives the outer boundary curve to touch each of the edges of the outer convex hull, while a third component keeps the inner boundary curve a minimum distance away from but inside the outer boundary curve. The components can be computed as a weighted sum:

$$C_m(m_i) = \alpha \cdot C_{curv}(m_i) + \beta \cdot C_{conv}(m_i) + \chi \cdot C_{cross}(m_i). \quad (5)$$

The actual regime under which the cost function of Equation (2) is optimized follows that of a Gauss-Seidel iteration. In each iteration, a specific group of parameters is updated conditioned on the tentative estimate of the remaining parameters from the previous iteration. For example, during the n-th iteration the vector of voxels x could be updated first, e.g. upon invoking a Conjugate Gradient (CG) step, conditioned on the tentative estimate of the models' parameters from the [n−1]-th iteration, while in a second step during the n-th iteration the models' parameters could be updated conditioned on the vector of voxels most recently updated. Variations of this approach are conceivable as well as other optimization techniques such as stochastic approaches, for example.

In one embodiment, $L_1$-Norm may be used instead of $L_2$-Norm in order to improve robustness of the method.

During each iteration, a gradient term of the cost function can be computed (step 1005). In one embodiment, the gradient of each term in the cost function can be separately computed and then summed up to obtain the overall gradient term of the cost function. In each iteration, two gradients can be calculated in an alternating manner: the gradient of cost function with respect to voxel array x and the gradient of cost function with respect to the parameter vector $m_i$. The gradient computation of cost function C( ) with respect to the voxel vector x is known in the art, for example, and can be carried out in the context of the CG method.

Going back to FIG. 10, based on the gradient of the cost function, the set of parameters $m_i$, i=0, . . . , $N_m$−1 can be adjusted (step 1006). In one embodiment, the voxel/pixel values x and the parameters $m_i$ can be adjusted alternately.

After both x and $m_i$ are adjusted, a value of the cost function of Equation (2) can be calculated (step 1007). In one embodiment, other values associated with the cost function can be calculated instead, such as the values of the gradients. The calculated value in step 1007 can be compared to an iteration stopping criteria (step 1008). The iteration stopping criteria can be set to measure if the iterations have converged. Once the cost function value is below the iteration stopping criteria (step 1008: Yes), the iterations can stop and the process may terminate. Otherwise, if the cost function value is above or equal to the iteration stopping criteria (step 1008: No), the next iteration can occur.

Figure 11:
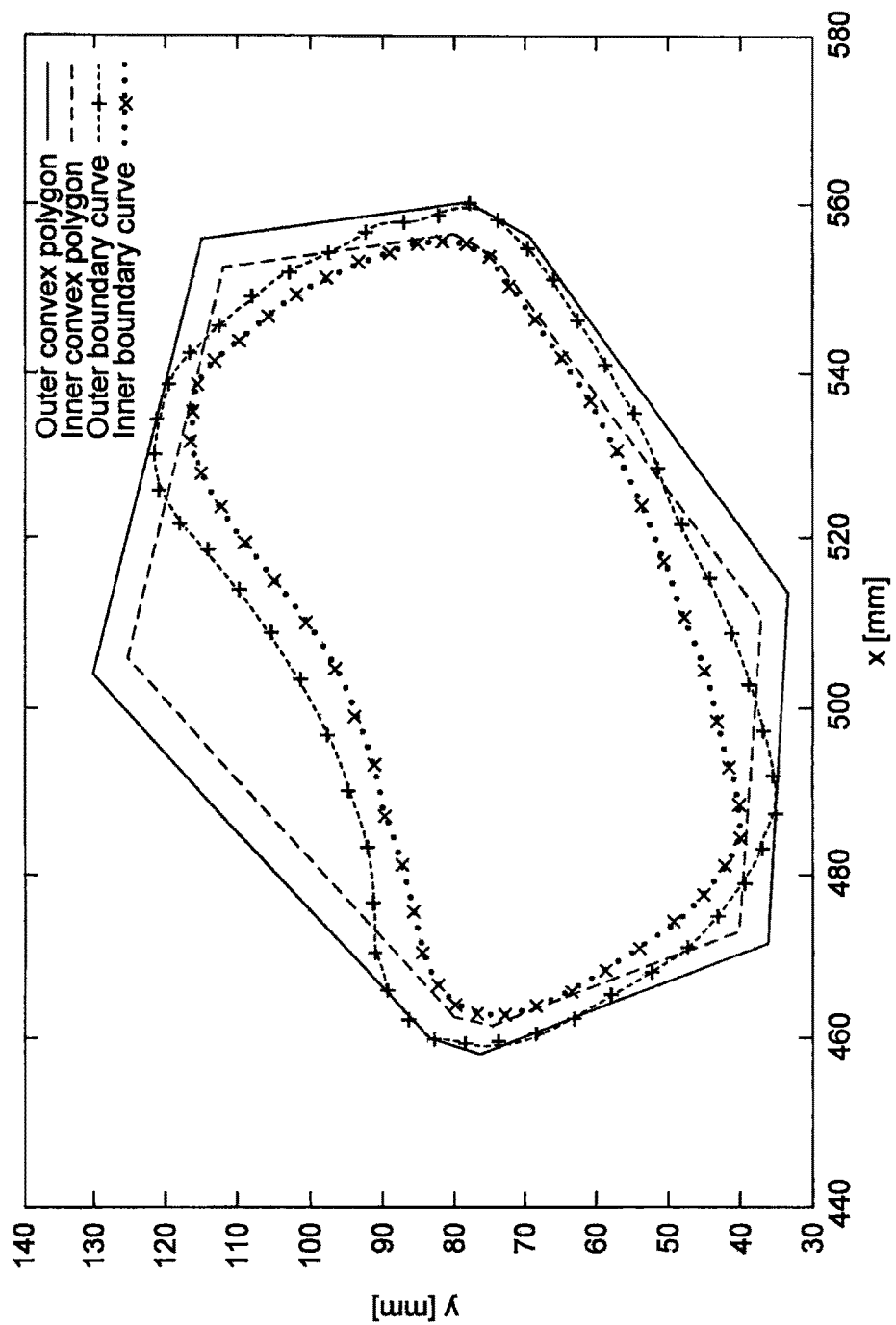
FIG. 11 shows a set of reconstructed boundary curves of a cashew nut shaped wine bottle, consistent with an exemplary disclosed embodiment.

FIG. 11 shows a set of reconstructed boundary curves of a cashew nut shaped wine bottle, consistent with an exemplary embodiment of the present disclosure. The convex polygons can be used to set the initial positions of points $\vec{p}$ on the outer and inner boundary curve, respectively. During the iterations, the positions of these points can be gradually adjusted to approach the real curvatures of the inner and outer boundaries of the object. Throughout the iterations, the curvatures can be bounded by the convex polygons, and the distance between the two curvatures must exceed a minimum threshold. As shown in FIG. 11, the resulted curvatures can exhibit a cashew nut shape.

It is contemplated that the steps associated with FIGS. 4 and 10 of the present invention can be implemented as a combination of hardware and software or in hardware alone. Furthermore, although certain aspects of the present invention are described as being stored in memory, one skilled in the art will appreciate that these aspects can also be stored on or read from other computer-readable media, such as secondary storage devices, like hard disks, floppy disks, or CD-Rom; or other forms of RAM or ROM. Moreover, although certain aspects of the present invention are described with regard to database instances associated with long-term storage, one skilled in the art will appreciate that the database instances can also be associated with memory records loaded into temporary storage, such as RAM.

INDUSTRIAL APPLICABILITY

The disclosed system and method can be applied to detect objects of interest using an automated or semi-automated process. Although disclosed embodiments are described in association with container, crate or baggage inspection such as at an airport, train station, cargo inspection or other port- and border-applications, the disclosed inspection system and inspection method can be used in other applications, such as medical imaging in a hospital or imaging facility, and product quality control in a factory, etc.

It will be apparent to those skilled in the art that various modifications and variations can be made in the disclosed system and method without departing from the scope of the disclosure. Additionally, other embodiments of the disclosed system and method will be apparent to those skilled in the art from consideration of the specification. It is intended that the specification and examples be considered as exemplary only, with a true scope of the disclosure being indicated by the following claims and their equivalents.

What is claimed is:

1. A method of modeling an item under x-ray inspection, comprising: acquiring scan data by performing a plurality of x-ray projections of the item with at least one x-ray projection source and receiving x-rays attenuated by the item from the at least one x-ray projection source at an x-ray detector array positioned to receive the attenuated x-rays; determining at least two closed boundary curves associated with the item based on the scan data, including a first closed boundary curve and a second closed boundary curve, wherein the second closed boundary curve lies entirely within the first closed boundary curve;

generating a parametric model of the item using the first closed boundary curve, the second closed boundary curve, and a set of material specific parameters comprising a first material specific parameter for a material both within the first closed boundary curve and outside the second closed boundary curve and a second material specific parameter for a material within the second closed boundary curve;

utilizing the parametric model to generate computed scan data;

adjusting the model of the item based on a comparison of the computed scan data and acquired scan data, by altering at least one of the set of: the at least two closed boundary curves and the set of material specific parameters; and displaying the parametric model of the item on a display device.

2. The method of claim 1, wherein the material both within the first closed boundary curve and outside the second closed boundary curve comprises a homogenous material.

3. The method of claim 1, wherein the first material specific parameter is an absorption coefficient $\mu$.

4. The method of claim 1, further comprising:
determining a goodness of fit based on the comparison of the computed scan data; and
determining if the goodness of fit satisfies a predetermined criterion.

5. The method of claim 4, wherein the goodness of fit is measured by a difference between the scan data and the computed scan data.

6. The method of claim 1, wherein altering the set of material specific parameters further comprises:
determining a cost function and a cost function gradient associated with the at least two closed boundary curves and the set of material specific parameters; and
altering the set of material specific parameters based on the cost function gradient.

7. The method of claim 1, wherein determining at least two closed boundary curves comprises:

determining a first maximum area based on the scan data;
determining at least one edge of the first maximum area;
determining a first closed boundary curve based on the at least one edge of the first maximum area;
determining a second maximum area based on the scan data, wherein the second maximum area is less than the first maximum area;
determining at least one edge of the second maximum area; and
determining a second closed boundary curve based on the at least one edge of the second maximum area.

8. The method of claim 7, wherein the first closed boundary curve is associated with an outer curvature of a container and wherein the second closed boundary curve is associated with an inner curvature of the container.

9. The method of claim 7, wherein each of the first material specific parameter and the second material specific parameter is an absorption coefficient $\mu$.

10. The method of claim 7, further comprising: determining a third boundary curve associated with the liquid level in the item, wherein the third boundary curve is at least one of: a closed boundary curve and an open boundary curve.

11. The method of claim 10, further comprising: determining a liquid volume utilizing the second closed boundary curve and the third boundary curve.

12. The method of claim 11, further comprising: comparing the liquid volume with a threshold, wherein the threshold is predetermined based on security regulations.

13. The method of claim 10, further comprising: comparing the second material specific parameter with a threshold, wherein the threshold is predetermined based on security regulations.

14. The method of claim 1, wherein determining at least two closed boundary curves further comprises:
defining a voxel array of a scan volume associated with the item;
determining a first area of the voxel array associated with a plurality of voxels outside the item;
determining a second area of the voxel array associated with a plurality of voxels co-positioned with the item;
setting the voxels of said second area to zero;
generating a parametric model of the scan volume using the first closed boundary curve, the first material specific parameter for the material both within the first closed boundary curve and outside the second closed boundary curve, and a second set of material specific parameters for the voxels of the first area, utilizing the model to generate computed scan data and comparing the computed scan data to the scan data, determining a goodness of fit, and
adjusting the parametric model of the scan volume by altering at least one of the set of: the at least two closed boundary curves, the first material specific parameter and the second set of material specific parameters.

15. The method of 14, wherein generating computed scan data further comprises:
generating a first subset of the computed scan data based on the voxel array; and
generating a second subset of the computed scan data based on the first closed boundary curve and the first material specific parameter.

16. The method of claim 7, wherein determining at least two closed boundary curves further comprises:
defining a voxel array of a scan volume associated with the item;
determining a first area of the voxel array associated with a plurality of voxels outside the item;

determining a second area of the voxel array associated with a plurality of voxels co-positioned with the item;

setting the voxels of said second area to zero;

generating a parametric model of the scan volume using the first closed boundary curve, the second closed boundary curve, the first material specific parameter for the material both within the first closed boundary curve and outside the second closed boundary curve, the second material specific parameter for the material within the second closed boundary curve and a third set of material specific parameters for the voxels of the first area, utilizing the parametric model to generate computed scan data and comparing the computed scan data to the scan data, determining a goodness of fit, and adjusting the parametric model of the scan volume by altering at least one of the set of: the first closed boundary curve, the second closed boundary curve, the first material specific parameter, the second material specific parameters and the third set of material specific parameters.

17. The method of claim 16, wherein the first closed boundary curve is associated with an outer curvature of a container and wherein the second closed boundary curve is associated with an inner curvature of the container.

18. The method of claim 16, wherein each of the first material specific parameter and the second material specific parameter is an absorption coefficient $\mu$ and the third set of material specific parameters is a set of absorption coefficients.

19. The method of claim 16, further comprising: determining a third boundary curve associated with the liquid level in the item, wherein the third boundary curve is at least one of:

a closed boundary curve and an open boundary curve.

20. The method of claim 19, further comprising determining a liquid volume utilizing the second closed boundary curve and the third boundary curve.

21. The method of claim 20, further comprising comparing the liquid volume with a threshold, wherein the threshold is predetermined based on security regulations.

22. The method of claim 19, further comprising: comparing the second material specific parameter with a threshold, wherein the threshold is predetermined based on security regulations.

23. An x-ray inspection system comprising: a scanner configured to acquire scan data by performing a plurality of x-ray projections of an item with at least one x-ray projection source and receiving x-rays attenuated by the item from the at least one x-ray projection source at an x-ray detector array positioned to receive the attenuated x-rays; and a processor configured to: determine at least two closed boundary curves associated with the item-based on the scan data, including a first closed boundary curve and a second closed boundary curve, wherein the second closed boundary curve lies entirely within the first closed boundary curve;

generate a parametric model of the item using the first closed boundary curve, the second closed boundary curve, and a set of material specific parameters comprising at least a first material specific parameter for a material both within the first closed boundary curve and outside the second closed boundary curve and a second material specific parameter for a material within the second closed boundary curve;

utilize the parametric model to generate computed scan data; and adjust the parametric model of the item based on a comparison between the computed scan data and the acquired scan data, by altering at least one of the set of: the at least two closed boundary curves and the set of material specific parameters.

24. The system of claim 23, wherein the material both within the first closed boundary curve and outside the second closed boundary curve comprises a homogenous material.

25. The system of claim 23, wherein the first material specific parameter is an absorption coefficient $\mu$.

26. The system of claim 23, wherein the processor is further configured to determine if the goodness of fit satisfies a predetermined criterion.

27. The system of claim 23, wherein the processor is configured to determine a goodness of fit measured by a difference between the scan data and the computed scan data.

28. The system of claim 23, wherein the processor is further configured to:

determine a cost function and a cost function gradient associated with the at least two closed boundary curves and the set of material specific parameters; and alter the set of material specific parameters based on the cost function gradient.

29. The system of claim 23, wherein the processor is further configured to:

determine a first maximum area based on the scan data;

determine at least one edge of the first maximum area;

determine a first closed boundary curve based on the at least one edge of the first maximum area;

determine a second maximum area based on the scan data, wherein the second maximum area is less than the first maximum area;

determine at least one edge of the second maximum area; and determine a second closed boundary curve based on the at least one edge of the second maximum area.

30. The system of claim 29, wherein the first closed boundary curve is associated with an outer curvature of a container and wherein the second closed boundary curve is associated with an inner curvature of the container.

31. The system of claim 29, wherein each of the first material specific parameter and the second material specific parameter is an absorption coefficient $\mu$.

32. The system of claim 29, wherein the processor is further configured to:

determine a third boundary curve associated with the liquid level in the item wherein the third boundary curve is at least one of: a closed boundary curve and an open boundary curve.

33. The system of claim 32, wherein the processor is further configured to:

determine a liquid volume utilizing the second closed boundary curve and the third boundary curve.

34. The system of claim 33, wherein the processor is further configured to:

compare the liquid volume with a threshold, wherein the threshold is predetermined based on security regulations.

35. The system of claim 32, wherein the processor is further configured to:

compare the second material specific parameter with a threshold, wherein the threshold is predetermined based on security regulations.

36. The system of claim 23, wherein the processor is further configured to:

define a voxel array of a scan volume associated with the item;

determine a first area of the voxel array associated with a plurality of voxels outside the item;
determine a second area of the voxel array associated with a plurality of voxels co-positioned with the item;
set the voxels of said second area to zero;
generate a parametric model of the scan volume using the first closed boundary curve, the first material specific parameter for the material both within the first closed boundary curve and outside the second closed boundary curve, and a second set of material specific parameters for the voxels of the first area, utilize the parametric model to generate computed scan data; and
compare the computed scan data to the scan data to determine a goodness of fit, and adjust the parametric model of the scan volume by altering at least one of the set of: the at least two closed boundary curves, the first material specific parameter and the second set of material specific parameters.

37. The system of 38, wherein the processor is further configured to:
generate a first subset of the computed scan data based on the voxel array; and
generate a second subset of the computed scan data based on the first closed boundary curve and the first material specific parameter.

38. The system of claim 29, wherein the processor configured to determine at least two closed boundary curves is further configured to:
define a voxel array of a scan volume associated with the item;
determine a first area of the voxel array associated with a plurality of voxels outside the item;
determine a second area of the voxel array associated with a plurality of voxels co-positioned with the item;
set the voxels of said second area to zero;
generate a parametric model of the scan volume using the first closed boundary curve, the second closed boundary curve, the first material specific parameter for the material both within the first closed boundary curve and outside the second closed boundary curve, the second material specific parameter for the material within the second closed boundary curve and a third set of material specific parameters for the voxels of the first area;
utilize the parametric model to generate computed scan data;
compare the computed scan data to the scan data to determine a goodness of fit; and
adjust the parametric model of the scan volume by altering at least one of the set of: the first closed boundary curve, the second closed boundary curve, the first material specific parameter, the second material specific parameters and the third set of material specific parameters.

39. The system of claim 38, wherein the first closed boundary curve is associated with an outer curvature of a container and wherein the second closed boundary curve is associated with an inner curvature of the container.

40. The system of claim 38, wherein each of the first material specific parameter and the second material specific parameter is an absorption coefficient $\mu$ and the third set of material specific parameters is a set of absorption coefficients.

41. The system of claim 38, wherein the processor is further configured to determine a third boundary curve associated with the liquid level in the item, wherein the third boundary curve is at least one of: a closed boundary curve and an open boundary curve.

42. The system of claim 41, wherein the processor is further configured to determine a liquid volume utilizing the second closed boundary curve and the third boundary curve.

43. The system of claim 42, wherein the processor is further configured to compare the liquid volume with a threshold, wherein the threshold is predetermined based on security regulations.

44. The system of claim 41, wherein the processor is further configured to compare the second material specific parameter with a threshold, wherein the threshold is predetermined based on security regulations.

45. A computer-readable medium comprising instructions stored thereon, wherein the instructions cause a computer to perform a method of modeling an item under x-ray inspection, the method comprising: acquiring scan data by performing a plurality of x-ray projections of the item with at least one x-ray projection source and receiving x-rays attenuated by the item from the at least one x-ray projection source at an x-ray detector array positioned to receive the attenuated x-rays; and
determining at least two closed boundary curves associated with the item based on the scan data, including a first closed boundary curve and a second closed boundary curve, wherein the second closed boundary curve lies entirely within the first closed boundary curve;
generating a parametric model of the item using the first closed boundary curve, the second closed boundary curve, and a set of material specific parameters comprising at least a first material specific parameter for a material both within the first closed boundary curve and outside the second closed boundary curve and a second material specific parameter for a material within the second closed curve;
utilizing the parametric model to generate computed scan data; and
adjusting the parametric model of the item based on a comparison of the computed scan data and acquired scan data, by altering at least one of the set of: the at least two closed boundary curves and the set of material specific parameters.

46. The computer-readable medium of claim 45, wherein the material both within the first closed boundary curve and outside the second closed boundary curve comprises a homogenous material.

47. The computer-readable medium of claim 45, wherein the first material specific parameter is an absorption coefficient $\mu$.

48. The computer-readable medium of claim 45, wherein the method further comprises:
determining a goodness of fit based on the comparison of the computed scan data; and
determining if the goodness of fit satisfies a predetermined criterion.

49. The computer-readable medium of claim 48, wherein the goodness of fit is measured by a difference between the scan data and the computed scan data.

50. The computer-readable medium of claim 45, wherein altering the set of material specific parameters further comprises:
determining a cost function and a cost function gradient associated with the at least two closed boundary curves and the set of material specific parameters; and
altering the set of material specific parameters based on the cost function gradient.

51. The computer-readable medium of claim 45, wherein determining at least two closed boundary curves comprises:
determining a first maximum area based on the scan data;
determining at least one edge of the first maximum area;
determining a first closed boundary curve based on the at least one edge of the first maximum, area;
determining a second maximum area based on the scan data, wherein the second maximum area is less than the first maximum area;
determining at least one edge of the second maximum area; and
determining a second closed boundary curve based on the at least one edge of the second maximum area.

52. The computer-readable medium of claim 51, wherein the first closed boundary curve is associated with an outer curvature of a container and wherein the second closed boundary curve is associated with an inner curvature of the container.

53. The computer-readable medium of claim 51, wherein each of the first material specific parameter and the second material specific parameter is an absorption coefficient μ.

54. The computer-readable medium of claim 51, wherein the method further comprises determining a third boundary curve associated with the liquid level in the item, wherein the third boundary curve is at least one of: a closed boundary curve and an open boundary curve.

55. The computer-readable medium of claim 54, wherein the method further comprises determining a liquid volume utilizing on the second closed boundary curve and the third boundary curve.

56. The computer-readable medium of claim 55, wherein the method further comprises comparing the liquid volume with a threshold, wherein the threshold is predetermined based on security regulations.

57. The computer-readable medium of claim 54, wherein the method further comprises comparing the second material specific parameter with a threshold, wherein the threshold is predetermined based on security regulations.

58. The computer-readable medium of claim 45, wherein determining at least one closed boundary curve further comprises:
defining a voxel array of a scan volume associated with the item;
determining a first area of the voxel array associated with a plurality of voxels outside the item;
determining a second area of the voxel array associated with a plurality of voxels co-positioned with the item;
setting the voxels of said second area to zero;
generating a parametric model of the scan volume using the closed boundary curve, the first material specific parameter for the first material both within the first closed boundary curve and outside the second closed boundary curve, and a second set of material specific parameters for the voxels of the first area, utilizing the parametric model to generate computed scan data and comparing the computed scan data to the scan data, determining a goodness of fit, and
adjusting the parametric model of the scan volume by altering at least one of the set of:
the at least two closed boundary curves, the first material specific parameter and the second set of material specific parameters.

59. The computer-readable medium of 58, wherein generating computed scan data further comprises:
generating a first subset of the computed scan data based on the voxel array; and
generating a second subset of the computed scan data based on the first closed boundary curve and the first material specific parameter.

60. The computer-readable medium of claim 51, wherein determining at least one closed boundary curve further comprises:
defining a voxel array of a scan volume associated with the item;
determining a first area of the voxel array associated with a plurality of voxels outside the item;
determining a second area of the voxel array associated with a plurality of voxels co-positioned with the item;
setting the voxels of said second area to zero;
generating a parametric model of the scan volume using the first closed boundary curve, the second closed boundary curve, the first material specific parameter for the material both within the first closed boundary curve and outside the second closed boundary curve, the second material specific parameter for the material within the second closed boundary curve and a third set of material specific parameters for the voxels of the first area, utilizing the parametric model to generate computed scan data and comparing the computed scan data to the scan data, determining a goodness of fit, and
adjusting the parametric model of the scan volume by altering at least one of the set of: the first closed boundary curve, the second closed boundary curve, the first material specific parameter, the second material specific parameters and the third set of material specific parameters.

61. The computer-readable medium of claim 60, wherein the first closed boundary curve is associated with an outer curvature of a container and wherein the second closed boundary curve is associated with an inner curvature of the container.

62. The computer-readable medium of claim 60, wherein each of the first material specific parameter and the second material specific parameter is an absorption coefficient μ and the third set of material specific parameters is a set of absorption coefficients.

63. The computer-readable medium of claim 60, wherein the method further comprises determining a third boundary curve associated with the liquid level in the item, wherein the third boundary curve is at least one of: a closed boundary curve and an open boundary curve.

64. The computer-readable medium of claim 63, wherein the method further comprises determining a liquid volume utilizing on the second closed boundary curve and the third boundary curve.

65. The computer-readable medium of claim 64, wherein the method further comprises comparing the liquid volume with a threshold, wherein the threshold is predetermined based on security regulations.

66. The computer-readable medium of claim 63, wherein the method further comprises comparing the second material specific parameter with a threshold, wherein the threshold is predetermined based on security regulations.

67. The method of claim 7, wherein the first maximum area is a polygon.

68. The system of claim 29, wherein the first maximum area is a polygon.

69. The computer-readable medium of claim 51, wherein the first maximum area is a polygon.

* * * * *

UNITED STATES PATENT AND TRADEMARK OFFICE
CERTIFICATE OF CORRECTION

PATENT NO. : 10,216,866 B2
APPLICATION NO. : 14/000907
DATED : February 26, 2019
INVENTOR(S) : Matthias Muenster and Pia Dreiseitel It is certified that error appears in the above-identified patent and that said Letters Patent is hereby corrected as shown below:

In the Claims

Claim 58, Column 19, Lines 53-54:
"the closed boundary curve, the first material specific parameter for the first material both within the first"
Should read:
--the first closed boundary curve, the first material specific parameter for the material both within the first--.

Signed and Sealed this
Fourteenth Day of May, 2019

Andrei Iancu
*Director of the United States Patent and Trademark Office*